(12) United States Patent
Walsh

(10) Patent No.: US 8,350,079 B2
(45) Date of Patent: Jan. 8, 2013

(54) TREPROSTINIL FORMULATION

(75) Inventor: David A. Walsh, Palmyra, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 487 days.

(21) Appl. No.: 12/437,054

(22) Filed: May 7, 2009

(65) Prior Publication Data

US 2009/0281189 A1    Nov. 12, 2009

Related U.S. Application Data

(60) Provisional application No. 61/051,509, filed on May 8, 2008.

(51) Int. Cl.
*A61K 31/19* (2006.01)
(52) U.S. Cl. .................................. 562/466; 514/573
(58) Field of Classification Search .................. None
See application file for complete search history.

(56) References Cited

U.S. PATENT DOCUMENTS

| | | | |
|---|---|---|---|
| 4,306,075 A | 12/1981 | Aristoff | |
| 5,153,222 A | 10/1992 | Tadepalli et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,700,025 B2 | 3/2004 | Moriarty et al. | |
| 6,756,033 B2 | 6/2004 | Cloutier et al. | |
| 6,765,117 B2 | 7/2004 | Moriarty et al. | |
| 6,803,386 B2 | 10/2004 | Shorr et al. | |
| 6,809,223 B2 | 10/2004 | Moriarty et al. | |
| 7,199,157 B2 | 4/2007 | Wade et al. | |
| 7,384,978 B2 | 6/2008 | Phares et al. | |
| 7,417,070 B2 | 8/2008 | Phares et al. | |
| 2005/0165111 A1 | 7/2005 | Wade et al. | |
| 2005/0282901 A1 | 12/2005 | Phares et al. | |
| 2005/0282903 A1 | 12/2005 | Wade et al. | |
| 2007/0078095 A1 | 4/2007 | Phares et al. | |
| 2008/0200449 A1 | 8/2008 | Olschewski et al. | |
| 2008/0249167 A1 | 10/2008 | Phares et al. | |
| 2008/0280986 A1 | 11/2008 | Wade et al. | |
| 2009/0036465 A1 | 2/2009 | Roscigno et al. | |

OTHER PUBLICATIONS

U.S. Appl. No. 12/334,731, filed Dec. 15, 2008, Batra et al.
Moriarty et al., "The Intramolecular Asymmetric Pauson-Khand Cyclization as a Novel and General Stereoselective Route to Benzindene Prostacyclins: Synthesis of UT-15 (Treprostinil)," *J. Org. Chem.* 2004, 69, 1890-1902.
Sorbera et al. "UT-15. Treatment of Pulmonary Hypertension Treatment of Peripheral Vascular Disease," *Drug of the Future*, 2001, 26(4), 364-374.

*Primary Examiner* — Yevegeny Valenrod
(74) *Attorney, Agent, or Firm* — Foley & Lardner LLP

(57) ABSTRACT

There is provided a stable monohydrate form of treprostinil and pharmaceutical formulation comprising the same, method of making and using the same.

11 Claims, 2 Drawing Sheets

TREPROSTINIL FORMULATION

RELATED APPLICATIONS

The present application claims priority to U.S. provisional application No. 61/051,509 filed May 8, 2008, which is incorporated herein in its entirety.

BACKGROUND

Prostacyclin derivatives are useful pharmaceutical compounds possessing activities such as platelet aggregation inhibition, gastric secretion reduction, lesion inhibition, and bronchodilation.

Treprostinil, the active ingredient in Remodulin®, was first described in U.S. Pat. No. 4,306,075. Treprostinil, and other prostacyclin derivatives have been prepared as described in Moriarty, et al in *J. Org. Chem.* 2004, 69, 1890-1902, *Drug of the Future,* 2001, 26(4), 364-374, U.S. Pat. Nos. 6,441,245, 6,528,688, 6,700,025, 6,809,223, 6,756,117 and U.S. patent application Ser. No. 12/334,731 filed on Dec. 15, 2008 to Batra et al.

U.S. Pat. No. 5,153,222 describes use of treprostinil for treatment of pulmonary hypertension. Treprostinil is approved for the intravenous as well as subcutaneous route, the latter avoiding septic events associated with continuous intravenous catheters. U.S. Pat. Nos. 6,521,212 and 6,756,033 describe administration of treprostinil by inhalation for treatment of pulmonary hypertension, peripheral vascular disease and other diseases and conditions. U.S. Pat. No. 6,803,386 discloses administration of treprostinil for treating cancer such as lung, liver, brain, pancreatic, kidney, prostate, breast, colon and head-neck cancer. U.S. patent application publication No. 2005/0165111 discloses treprostinil treatment of ischemic lesions. U.S. Pat. No. 7,199,157 discloses that treprostinil treatment improves kidney functions. U.S. patent application publication No. 2005/0282903 discloses treprostinil treatment of neuropathic foot ulcers. U.S. Patent application publication No. 2008/0280986 discloses treprostinil treatment of pulmonary fibrosis. U.S. Pat. No. 6,054,486 discloses treatment of peripheral vascular disease with treprostinil. U.S. Patent application publication No. 2009/0036465 discloses combination therapies comprising treprostinil. U.S. Patent application publication No. 2008/0200449 discloses delivery of treprostinil using a metered dose inhaler. U.S. Patent application publication No. 2008/0280986 discloses treatment of interstitial lung disease with treprostinil and treatment of asthma with treprostinil. U.S. Pat. Nos. 7,417,070 and 7,384,978 as well as U.S. publications Nos. 2007/0078095, 2005/0282901 and 2008/0249167, describe oral formulations of treprostinil and other prostacyclin analogs.

The teachings of the aforementioned references are incorporated by reference to show how to practice the embodiments of the present invention.

In sum, treprostinil is of great importance from a medicinal point of view. Therefore, a need exists for a stable form of treprostinil which presents advantage in storage, shipment, handling, and formulation, for example.

SUMMARY OF THE INVENTION

One embodiment of the present invention relates to a monohydrate of treprostinil, a pharmaceutical formulation comprising treprostinil monohydrate, and methods of making and using the same.

The monohydrate is stable at room temperature over a longer period of time than other forms of treprostinil.

In one embodiment, there is provided a pharmaceutical formulation comprising a therapeutically effective amount of treprostinil monohydrate and a pharmaceutically acceptable carrier therefore.

In one embodiment, there is provided a process for preparing treprostinil monohydrate.

In one embodiment, there is further provided a method of using treprostinil monohydrate in treating medical conditions, including those for which it is known in the art to use treprostinil, such as those described in aforementioned J. Org. Chem. 2004, 69, 1890-1902, Drug of the Future, 2001, 26(4), 364-374, U.S. Pat. Nos. 5,153,222, 6,054,486, 6,521,212, 6,756,033, 6,803,386, and 7,199,157, U.S. patent application publication Nos. 2005/0165111, 2005/0282903, 2008/0200449, 2008/0280986 and 2009/0036465.

DETAILED DESCRIPTION

Figure 1A:
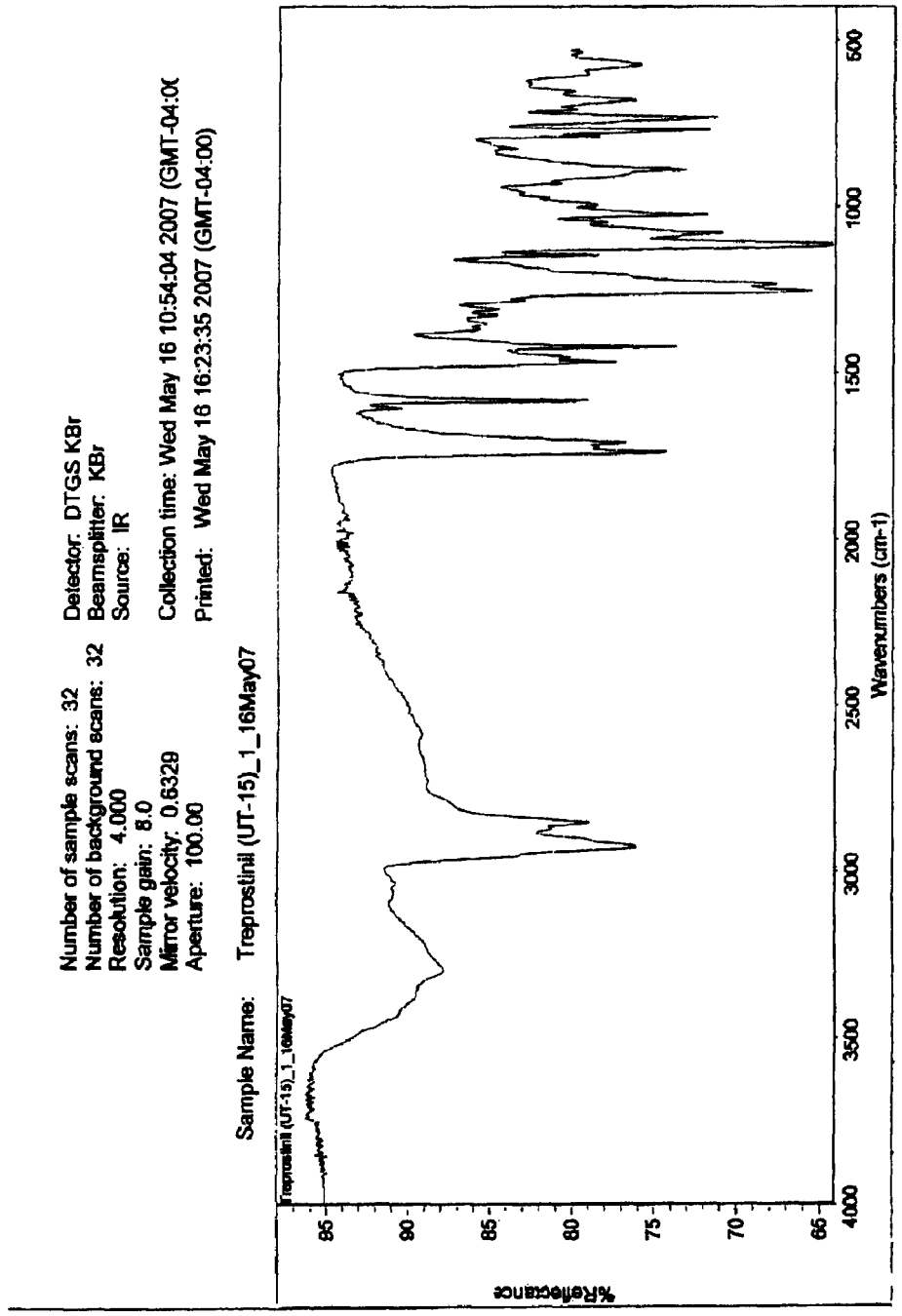
FIG. 1a is an IR (infrared) spectrum of anhydrous treprostinil.
Figure 1B:
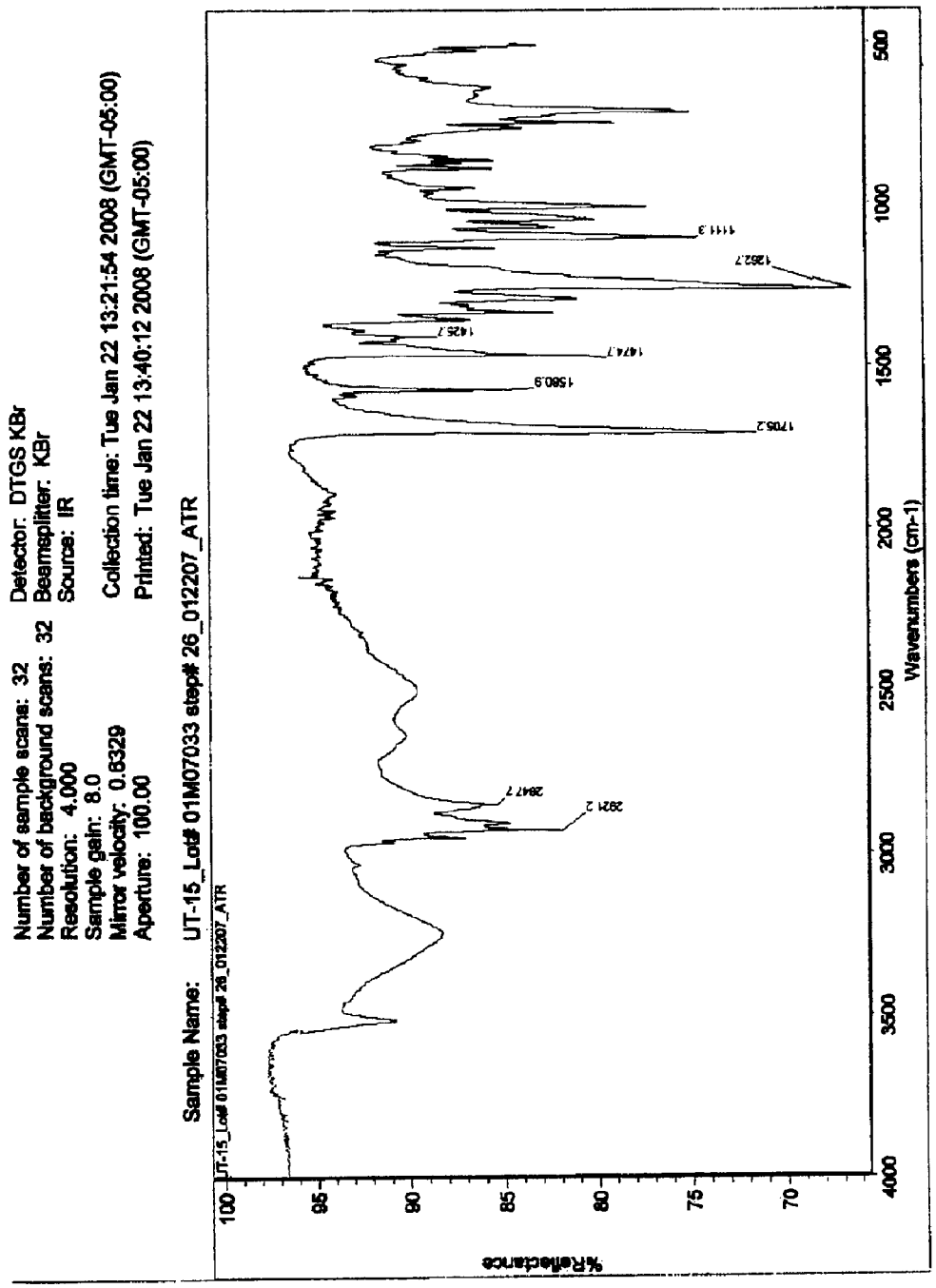
FIG. 1b is an IR (infrared) spectrum of treprostinil monohydrate.

Unless otherwise specified, "a" or "an" means "one or more". The present invention relates to a novel monohydrate form of treprostinil. Treprostinil is the active ingredient of Remodulin®, which has been approved by the U.S. FDA for the treatment of Pulmonary Arterial Hypertension (PAH) in patients with NYHA Class II, III and IV symptoms to diminish symptoms associated with exercise using subcutaneous or intravenous administration.

Treprostinil's chemical name is 2-((1R,2R,3aS,9aS)-2-hydroxy-1-((S)-3-hydroxyoctyl)-2,3,3a,4,9,9a-hexahydro-1H-cyclopenta[b]naphthalen-5-yloxy)acetic acid of the following structure:

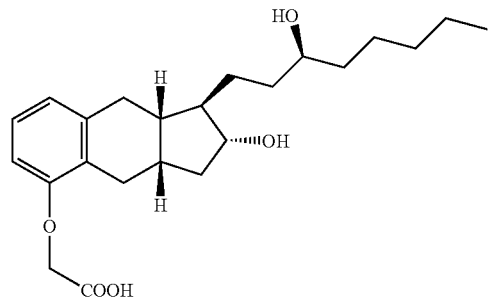 [SMILES: CCCCC[C@H](O)CC[C@@H]1[C@H]2Cc3cccc(OCC(=O)O)c3C[C@H]2C[C@H]1O]

The anhydrous form of treprostinil (TREPROSTINIL) has been previously described, e.g., in *J. Org. Chem.* 2004, 69, 1890-1902. The anhydrous form is not stable at room temperature. Stability tests show that the anhydrous TREPROSTINIL is not stable at 25° C. and dimers formed upon standing. A larger amount of dimers can form at higher temperatures. However, dimer formation is negligible at 5° C. Therefore, anhydrous treprostinil must be refrigerated for storage and transport. In the past, treprostinil had to be refrigerated and shipped with ice packs to maintain low (2° C.-8° C.) temperatures.

The instability of anhydrous treprostinil also imposes challenges to its preparation. To obtain anhydrous treprostinil, wet compound from recrystallization was heated in a vacuum. It was found that if the treprostinil solid was heated above 50° C., two dimers of treprostinil formed as impurities in the solid. Therefore, heating temperature must be carefully controlled to avoid high heat when drying treprostinil in order to remove all water, otherwise these two dimer impurities will be produced.

In addition to instability, the anhydrous treprostinil is difficult to handle. The anhydrous form is a fine, fly-away material that is difficult to weigh because of the static electrical charge that it produces. Because treprostinil is a potent prostaglandin analogue that has strong biological activity, analysts and operators must use extreme caution when handling this material to avoid exposure.

It has now surprisingly been found that treprostinil can exist in a monohydrate form. Data has been generated to characterize a monohydrate form of treprostinil. One advantage of the monohydrate is that it is stable at room temperature. Stability data show that the monohydrate form is more stable than the anhydrous form at room temperature, e.g. 25° C. Treprostinil monohydrate can be stored and shipped with no special handling. The stability of treprostinil has been significantly improved, such that it no longer needs to be stored in a refrigerator or shipped under cold conditions.

The second advantage of the monohydrate is that it is much easier to weigh and handle the material because the static electrical charge is greatly reduced in this form. It is much easier for personnel to avoid exposure when working with the monohydrate form. Thus, the safety in handling the material has also been improved because of the improved physical properties of the mono-hydrate.

Because of its stability and safety, monohydrate treprostinil also presents advantages for use in pharmaceutical formulations.

In one embodiment of the present invention, there is provided a monohydrate form of treprostinil. In one embodiment, the treprostinil monohydrate is in crystalline form. In one embodiment, the treprostinil monohydrate is in a form having a purity of at least 90% by weight of the composition. In one embodiment, the treprostinil monohydrate in a form having a purity of at least 95% by weight of the composition. In one embodiment, the treprostinil monohydrate has a purity of at least 99% by weight of the composition.

The treprostinil monohydrate is stable at room temperature, and further exhibits stability across a range of temperatures from about 15° C. to about 35° C., and more preferably from about 20° C. to about 30° C.

In one embodiment, there is provided a process for the preparation of treprostinil monohydrate, said process comprising
 a. recrystallizing anhydrous or wet treprostinil from an organic solvent/water combination to provide a solid; and
 b. air-drying the solid at ambient temperature until no additional solvents evaporate.

The temperature for air-drying in the above process is preferably from about 15° C. to about 35° C., and more preferably from about 20° C. to about 30° C. The anhydrous or wet treprostinil being recrystallized may have a range of purity. In some embodiments, it is pure. In some embodiments, it is substantially pure. In some embodiments, it may be crude product from the synthesis. In some embodiment, the crude product of treprostinil may be solid or semisolid.

In some embodiments, the organic solvent may be water soluble solvent including but not limited to lower alcohol, lower ketone, and lower ether. The lower alcohol may be methanol, ethanol, or isopropanol for example. The lower ketone may be acetone, for example. Lower ether may be tetrahydrofuran or dioxane, for example. The ratio of organic solvent/water may be about 1:1, or about 1:2, or about 1:3, or about 1:4, or about 1:5, or about 2:1, or about 3:1, or about 4:1, or about 5:1. In one embodiment, the organic solvent is ethanol. In one embodiment, the ratio of organic solvent/water is 1:1.

One embodiment of the invention is treprostinil monohydrate prepared according to the aforementioned process.

Another embodiment is a pharmaceutical formulation comprising treprostinil monohydrate and a pharmaceutically acceptable carrier or excipient.

The term "pharmaceutical" when used herein as an adjective means substantially non-deleterious to the recipient mammal. By "pharmaceutical formulation" it is meant the carrier, diluent, excipients and active ingredient(s) must be compatible with the other ingredients of the formulation, and not deleterious to the recipient thereof.

Treprostinil monohydrate can be formulated prior to administration. The selection of the formulation should be decided by the attending physician taking into consideration the same factors involved with determining the effective amount.

The total active ingredients in such formulations comprises from 0.1% to 99.9% by weight of the formulation. Treprostinil monohydrate can be formulated with one or more additional active ingredients or as the sole active ingredient.

Pharmaceutical formulations of the present invention are prepared by procedures known in the art using well known and readily available ingredients. For example, treprostinil monohydrate, either alone, or in combination with other active ingredient(s) are formulated with common excipients, diluents, or carriers, and formed into tablets, capsules, suspensions, solutions, injectables, aerosols, powders, and the like.

Pharmaceutical formulations of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral formulations may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, treprostinil monohydrate is mixed with at least one inert, pharmaceutical carrier such as sodium citrate, or dicalcium phosphate, and/or (a) fillers or extenders such as starches, sugars including lactose and glucose, mannitol, and silicic acid, (b) binding agents such as carboxymethyl-cellulose and other cellulose derivatives, alginates, gelatin, poly(vinylpyrrolidine), sucrose and acacia, (c) humectants such as glycerol, (d) disintegrating agents such as agar-agar, calcium carbonate, sodium bicarbonate, potato or tapioca starch, alginic acid, silicates and sodium carbonate, (e) moisturizing agents such as glycerol; (f) solution retarding agents such as paraffin, (g) absorption accelerating agents such as quaternary ammonium compounds, (h) wetting agents such as cetyl alcohol and glycerin monostearate, (i) absorbents such as kaolin and bentonite clay, and (j) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid formulations of a similar type may also comprise the fill in soft or hard gelatin capsules using excipients such as lactose as well as high molecular weight poly(ethylene glycols) and the like. Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract. The active ingredient(s) may also be microencapsulated in a sustained-release coating, with the microcapsules being made part of a pill of capsule formulation.

Liquid dosage forms for oral administration of monohydrate treprostinil include solution, emulsions, suspensions, syrups and elixirs. In addition to the active components, liquid formulations may include inert diluents commonly used in the art such as water or other pharmaceutical solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof. Besides inert diluents, the liquid oral formulations may also include adjuvants such as wetting agents, emulsifying and suspending agents, and sweetening, flavoring, and perfuming agents. Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

Another embodiment is a method of treating a medical condition comprising administering a therapeutically effective amount of the aforementioned pharmaceutical formulation comprising the treprostinil monohydrate to a subject in need thereof. The medical conditions being treated include but not limited to pulmonary hypertension (including primary and secondary pulmonary hypertension and pulmonary arterial hypertension), congestive heart failure, peripheral vascular disease, asthma, severe intermittent claudication, immunosuppression, proliferative diseases, cancer such as lung, liver, brain, pancreatic, kidney, prostate, breast, colon and head-neck cancer, ischemic lesions, neuropathic foot ulcers, and pulmonary fibrosis, kidney function, and interstitial lung disease. In some embodiments, the pharmaceutical formulation may comprise one or more active ingredients in addition to treprostinil monohydrate. The following references are incorporated by reference for practicing the embodiments of the present invention. *J. Org. Chem.* 2004, 69, 1890-1902, *Drug of the Future,* 2001, 26(4), 364-374, U.S. Patent Nos. 5,153,222, 6,054,486, 6,521,212, 6,756,033, 6,803,386, and 7,199,157, U.S. patent application publication Nos. 2005/0165111, 2005/0282903, 2008/0200449, 2008/0280986 and 2009/0036465.

The invention will now be described in reference to the following Examples. These examples are not to be regarded a limiting the scope of the present invention, but shall only serve in an illustrative manner.

EXAMPLE

I. Preparation:

TREPROSTINIL was recrystallized from a 50% aqueous solution of ethanol. The "wet" solid was collected by filtration and air-dried at ambient temperature until no additional solvents evaporate. The monohydrate was the result of this drying process.

II. Stability of Anhydrous Form Versus Monohydrate Form of TREPROSTINIL at 25° C.

1. Stability Report (6-month) for anhydrous lot #01A07002

The anhydrous treprostinil was prepared according to the following procedure.

A 3.34-kg sample of treprostinil diethanolamine salt was dissolved in 40 L of sterile water, 60 L of ethyl acetate and 3.2 L of 3 M HCl were added and the mixture stirred. The layers were separated and the aqueous layer was extracted thrice with 20-L portions of ethyl acetate. The four organic layers were combined, the organic solution washed twice with 20-L portions of sterile water, once with 20 L of brine and dried over 2.97 kg of anhydrous sodium sulfate. The mixture was filtered and the filtrate was concentrated to yield treprostinil as a gummy solid. This solid was transferred to glass drying trays and let air-dry for 93 hours. This solid was then dissolved in 23.4 kg of ethanol, warmed to 48° C. and treated with 23.4 kg of warm (40-50° C.) sterile water. The solution was stirred and then stirring was stopped to allow the treprostinil to slowly crystallize. The resulting white solid was collected by filtration in an Aurora filter, washed with 45 L of a cold (6° C.) 20% ethanol in sterile water solution, the filter moved to a Hepa-filtered Finishing Room and the solid dried under house vacuum for 22.3 hours. The solid was transferred to drying trays and further dried in a vacuum oven at 55 deg. C and 0.26 Torr for 22.7 hours to give 2.63 kg (96.3%) of anhydrous treprostinil (Lot #01A07002) as a white solid.

| Stability Data for Treprostinil (TREPROSTINIL) at 25° C. Lot No. 01 A07002 (Anhydrous) | | | |
| --- | --- | --- | --- |
| Test | Initial | 3 months | 6 months |
| Physical examination | White powder | White powder | White powder |
| Water (Karl Fischer) | 0.4% | 0.7% | 0.8% |
| HPLC Assay | | | |
| Treprostinil | 99.6% | 98.1% | 95.4% |
| 750W93 | 0.2 | 1.2 | 1.5 |
| 751W93 | 0.3 | 0.9 | 1.1 |

2. UT Stability Summary (18-month) for monohydrate lot # D-1007-089

The treprostinil monohydrate was prepared according to the following procedure.

A 3.4-kg sample of treprostinil diethanolamine salt was dissolved in 36 L of sterile water, 60 L of ethyl acetate and 3.6 L of 3 M HCl were added and the mixture stirred. The layers were separated and the aqueous layer was extracted thrice with 20-L portions of ethyl acetate. The four organic layers were combined, the organic solution washed twice with 20-L portions of sterile water, once with 20 L of brine and dried over 2.86 kg of anhydrous sodium sulfate. The mixture was filtered and the filtrate was concentrated to yield treprostinil as a gummy solid. This solid was transferred to glass drying trays and let air-dry for 66 hours. This solid was then dissolved in 23.8 kg of ethanol, warmed to 48° C. and treated with 23.8 kg of warm (40-50° C.) sterile water. The solution was stirred and then stirring was stopped to allow the treprostinil to slowly crystallize. The resulting white solid was collected by filtration in an Aurora filter, washed with 45 L of a cold (6° C.) 20% ethanol in sterile water solution, the filter moved to a Hepa-filtered Finishing Room and the solid dried under house vacuum for 23 hours. The solid was transferred to glass drying trays and further air-dried for 115 hours until the total weight of the material was constant (no further solvent loss). A sample of this treprostinil monohydrate was taken as Lot #D-1007-089 for stability studies. The remaining material was further dried in a vacuum oven at 55° C. and 1.66 Torr for 10 hours to give 2.68 kg (96.4%) of anhydrous treprostinil (Lot #01G07018).

Study of Effects on Extended Room Temperature Drying of In-Process Sample for Water Content, Melting Point and Assay/Impurity Profile
Sample: TREPROSTINIL Lot# D-1007-089, two containers 1 & 2; #1 is closed; #2 is covered with Kimwipe; both kept at room temperature

|  | Initial Container 1 | Initial Container 2 | 1 Month Container 1 | 1 Month Container 2 | 2 Months Container 1 | 2 Months Container 2 |
| --- | --- | --- | --- | --- | --- | --- |
| Water, KF | 4.55% | 4.37% | NT | NT | 4.46% | 4.47% |
| Melting Point | 122.5-124.0 | 122.5-123.5 | NT | NT | 122.5-125.5 | 122.5-123.0 |
| TREPROSTINIL Assay | 99.6 | 99.5 | 100.1 | 100.4 | 99.5 | 99.6 |
| TREPROSTINIL Ethyl Ester | 0.2 | 0.2 | 0.2 | 0.2 | 0.2 | 0.2 |
| 750W93 | 0.1 | 0.1 | 0.09 | 0.09 | 0.09 | 0.09 |
| 751W93 | 0.04 | 0.04 | 0.04 | 0.04 | 0.04 | 0.04 |
| Impurity 1 | 0.06 | 0.05 | 0.05 | 0.05 | 0.05 | 0.05 |
| Impurity 2 | 0.05 | <0.05 | 0.05 | 0.05 | 0.05 | 0.05 |
| Total impurities | 0.5 | 0.5 | 0.5 | 0.5 | 0.5 | 0.5 |

|  | 3 Months Container 1 | 3 Months Container 2 | 6 Months Container 1 | 6 Months Container 2 |
| --- | --- | --- | --- | --- |
| Water, KF | 4.51% | 4.48% | 4.59% | 4.72% |
| Melting Point | 122.0-123.0 | 122.5-123.5 | 122.0-123.0 | 122.0-123.5 |
| TREPROSTINIL Assay | 98.1 | 98.6 | 99.4 | 99.3 |
| TREPROSTINIL Ethyl Ester | 0.2 | 0.2 | 0.2 | 0.2 |
| 750W93 | 0.09 | 0.09 | 0.1 | 0.09 |
| 751W93 | 0.04 | 0.04 | 0.04 | 0.04 |
| Impurity 1 | 0.06 | 0.06 | <0.05 | <0.05 |
| Impurity 2 | <0.05 | <0.05 | <0.05 | <0.05 |
| Total impurities | 0.5 | 0.5 | 0.6 | 0.6 |

|  | 12 Months Container 1 | 12 Months Container 2 | 18 Month Container 1 | 18 Month Container 2 |
| --- | --- | --- | --- | --- |
| Water, KF | 4.72% | 4.73% | 4.67% | 4.72% |
| Melting Point | 123.0-124.0 | 123.0-124.0 | 123.0-124.0 | 123.0-124.0 |
| TREPROSTINIL Assay | 100.1 | 100.3 | 100.3 | 99.8 |
| TREPROSTINIL Ethyl Ester | 0.2 | 0.2 | 0.2 | 0.2 |
| 750W93 | 0.09 | 0.09 | 0.09 | 0.09 |
| 751W93 | <0.05 | <0.05 | <0.05 | <0.05 |
| Impurity 1 | 0.06 | 0.06 | <0.05 | <0.05 |
| Impurity 2 | 0.05 | 0.05 | 0.05 | 0.05 |
| Total impurities | 0.5 | 0.05 | 0.05 | 0.05 |

Stability data collected on TREPROSTINIL lot D-1007-089 shows that the monohydrate is more stable than the anhydrous form at ambient temperatures. One of the stability studies has followed the monohydrate of TREPROSTINIL stored in an open container. The one mole of water has not disappeared from the solid over 18-months indicating that the water is an integral part of the crystalline structure, and the material is not just a "wet" solid.

III. Accelerated Stability Data at 30 and 40° C. (Lot #01M07033).

In the present experiment, 500 mg Treprostinil monohydrate samples were stored in Nalgene 125 ml, HDPE bottles. The experimental procedure used in this experiment was the same as the described above procedure for lot D-1007-089.

|  | Initial | 3-Months 25° C./ 60% RH | 3-Months 30° C./ 65% RH | 3-Months 40 C./ 75% RH |
|---|---|---|---|---|
| Water, KF | 4.5% | 4.8% | 4.8% | 4.8% |
| Melting Point | 123.0-124.0° C. | N.T. | N.T. | N.T. |
| Specific Rotation | 45.5° | N.T. | N.T. | N.T. |
| UT-15 Assay | 98.7% | 99.5% | 99.5% | 99.4% |
| 3AU90 | 0.1% | <0.05% | <0.05% | <0.05% |
| UT-15 Ethyl Ester | 0.2% | 0.2% | 0.2% | 0.2% |
| 750W93 | 0.08% | 0.07% | 0.07% | 0.08% |
| 751W93 | <0.05% | <0.05% | <0.05% | <0.05% |
| Impurity 1 (RRT: 0.58) | NR | 0.05% | 0.05% | 0.05% |
| Total Impurities | 0.4% | 0.4% | 0.4% | 0.4% |

|  | 6-Months[1] 25° C./60% RH | 6-Months[1] 30° C./65% RH | 6-Months[1] 40 C./75% RH |
|---|---|---|---|
| Water, KF | 4.7% | 4.7% | 4.7% |
| Melting Point | 123.0-123.5° C. | 123.0-123.5° C. | 123.0-123.5° C. |
| Specific Rotation | 45.3° | 45.9° | 45.6° |
| UT-15 Assay | 99.0% | 99.1% | 99.7% |
| 3AU90 | 0.06% | 0.06% | 0.07% |
| UT-15 Ethyl Ester | 0.2% | 0.2% | 0.2% |
| 750W93 | 0.07% | 0.07% | 0.09% |
| 751W93 | <0.05% | <0.05% | 0.05% |
| Impurity 1 (RRT: 0.58) | NR | NR | NR |
| Total Impurities | 0.4% | 0.4% | 0.4% |

|  | 12-Months 25° C./60% RH | 12-Months 40 C./75% RH |
|---|---|---|
| Water, KF | 4.7% | 4.8% |
| Melting Point | 122.5-123.0° C. | 123.0-123.5° C. |
| Specific Rotation | 45.5° | 46.7° |
| UT-15 Assay | 99.8% | 98.6% |
| 3AU90 | <0.05% | <0.05% |
| UT-15 Ethyl Ester | 0.2% | 0.2% |
| 750W93 | 0.08% | 0.09% |
| 751W93 | <0.05% | 0.05% |
| Impurity 1 (RRT: 0.58) | 0.06% | 0.05% |
| Total Impurities | 0.4% | 0.4% |

Notes:
[1]30° C./65% RH: Study discontinued at 6 months;
40° C./75% RH: study discontinued at 12 months..

IV. Characterization of the Anhydrous Form and the Monohydrate Form

The characterization was done by the following method:
1. Determination of water content by Karl Fischer method,
2. Melting point,
3. HPLC assay,
4. Specific rotation,
5. IR spectroscopy,
6. Elemental analysis.

One mole of water in TREPROSTINIL calculates to 4.41% by weight and these results confirm that there is one mole of water present in this hydrated form of TREPROSTINIL.

A comparison of monohydrated and anhydrous forms of treprostinil (TREPROSTINIL) was done. In the course of the preparation of TREPROSTINIL, lot number 01 M07033 was air-dried for several hours until no weight-loss was observed. Data was collected on the monohydrate form. The solid was then vacuum-dried at 55° C. for several hours. Data was then collected on the anhydrous form.

| Data Summary for a Comparison of Mono-Hydrated and Anhydrous Forms of Treprostinil (TREPROSTINIL) (Lot No. 01 M07033) | | |
|---|---|---|
| Test | MonoHydrate | Anhydrous |
| Physical examination | White powder | White powder |
| Melting point range | 123.0 to 124.0° C. | 122.0 to 123.1° C. |
| Specific rotation | +45.5° at 589 nm and 25° C. | +46.0° at 589 nm and 25° C. |
| Water (Karl Fischer) | 4.5% w/w | 0.8% w/w |
| HPLC Assay | | |
| Treprostinil | 98.7% (adjusted for water) | 99.8% (adjusted for water) |
| 1AU90 | ND | ND |
| 2AU90 | ND | ND |
| 97W86 | ND | ND |
| 3AU90 | 0.1% w/w | 0.2% w/w |
| Methyl ester | ND | ND |
| Ethyl ester | 0.2% w/w | 0.2% w/w |
| 750W93 | 0.08% w/w | 0.09% w/w |
| 751W93 | <0.05% w/w | <0.05% w/w |
| Total Related Substances | 0.4% w/w | 0.5% w/w |

ND = not detected

The above table indicates that the only discernable difference between the two forms of TREPROSTINIL is the amount of water present. A 4.5% water result by Karl Fischer assay for the hydrated form corresponds to one mole of water present. The IR spectrum of the monohydrate form is different than the IR spectrum of the anhydrous form of TREPROSTINIL, which is an indication that the monohydrate is a distinct molecular entity. Elemental analyses were performed on the anhydrous form and the monohydrate form. The C and H combustion analysis results for the mono-hydrate (lot no. 01M07033) are: Analysis calculated for $C_{23}H_{34}O_5 \cdot H_2O$ (M.W. 408.499): C, 67.63; H, 8.87. Found: C, 67.74; H, 8.79. The C and H combustion analysis results for the anhydrous reference standard (lot no. D-066-193) are: Analysis calculated for $C_{23}H_{34}O_5$ (M.W. 390.486): C, 70.75; H, 8.77. Found: C, 70.58; H, 9.07.

Although the foregoing refers to particular embodiments, it should be understood that the present invention is not so limited. It will occur to those of ordinary skill in the art that various modifications may be made to the disclosed embodiments and that such modifications are intended to be within the scope of the present invention. All publications and patents referenced herein are hereby incorporated by reference in their entirety to the same extent as if each was individually incorporated by reference.

What is claimed is:

1. A dry solid product comprising a monohydrate form of treprostinil.

2. A dry solid product comprising a treprostinil monohydrate, wherein the monohydrate constitutes at least 90% by weight of the product.

3. A dry solid product comprising a treprostinil monohydrate, wherein the treprostinil monohydrate is in crystalline form.

4. A process for preparing treprostinil monohydrate, said process comprising
   a. recrystallizing anhydrous or wet treprostinil from an organic solvent/water combination to provide a solid; and
   b. air-drying the solid at a temperature from about 15° C. to about 35° C. until no additional solvent evaporates.

5. The process of claim 4, wherein the temperature of air-drying is from about 20° C. to about 30° C.

6. The process of claim 4, wherein the organic solvent is selected from the group consisting of a lower alcohol, a lower ketone, and a lower ether.

7. The process of claim 6, wherein the organic solvent is ethanol.

8. The process of claim 4, wherein the ratio of the organic solvent/water is about 1:1, or about 1:2, or about 1:3, or about 1:4, or about 1:5, or about 2:1, or about 3:1, or about 4:1, or about 5:1.

9. The process of claim 7, wherein the ratio of ethanol/water is about 1:1.

10. A dry solid product comprising a monohydrate treprostinil produced by the process according to claim 9.

11. A method of storing or shipping treprostinil comprising storing or shipping treprostinil as a dry solid product comprising a monohydrate form of treprostinil.

* * * * *

UNITED STATES PATENT AND TRADEMARK OFFICE
CERTIFICATE OF CORRECTION

| | | |
|---|---|---|
| PATENT NO. | : 8,350,079 B2 | Page 1 of 1 |
| APPLICATION NO. | : 12/437054 | |
| DATED | : January 8, 2013 | |
| INVENTOR(S) | : David A. Walsh | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 535 days.

Signed and Sealed this
Twenty-eighth Day of May, 2013

Teresa Stanek Rea
*Acting Director of the United States Patent and Trademark Office*